United States Patent [19]
Pollak et al.

[11] Patent Number: 5,858,327
[45] Date of Patent: Jan. 12, 1999

[54] HYDRAZINO-TYPE $N_2S_2$ RADIONUCLIDE CHELATING COMPOUNDS

[75] Inventors: Alfred Pollak, Ontario; Robert Kirby, St. Rosemere; Robert Dunn-Dufault, Ontario, all of Canada

[73] Assignee: Resolutions Pharmaceuticals, Inc., Mississagwa, Canada

[21] Appl. No.: 613,121

[22] Filed: Mar. 8, 1996

Related U.S. Application Data

[60] Continuation-in-part of Ser. No. 274,850, Jul. 14, 1994, Pat. No. 5,574,140, which is a division of Ser. No. 116,504, Sep. 3, 1993, abandoned.

[51] Int. Cl.⁶ .................................................. A61K 51/04
[52] U.S. Cl. .......................... 424/1.65; 564/35; 564/18; 534/10; 534/14
[58] Field of Search ................. 564/35, 18; 534/10, 534/14, 15, 16; 424/1.65, 1.69; 530/300, 350

[56] References Cited

U.S. PATENT DOCUMENTS

| | | | |
|---|---|---|---|
| 4,849,511 | 7/1989 | Verbruggen | 534/14 |
| 4,861,869 | 8/1989 | Nicolotti et al. | 530/402 |
| 4,897,255 | 1/1990 | Fritzberg et al. | 424/1.1 |
| 4,965,392 | 10/1990 | Fritzberg et al. | 558/254 |
| 4,980,147 | 12/1990 | Fritzberg et al. | 424/1.1 |
| 5,037,630 | 8/1991 | Fritzberg et al. | 424/1.1 |
| 5,082,930 | 1/1992 | Nicolotti et al. | 530/402 |
| 5,089,249 | 2/1992 | Fritzberg et al. | 424/1.1 |
| 5,091,514 | 2/1992 | Fritzberg et al. | 534/14 |
| 5,112,594 | 5/1992 | Woulfe et al. | 424/1.1 |
| 5,112,595 | 5/1992 | Woulfe et al. | 424/1.1 |
| 5,112,953 | 5/1992 | Gustavson et al. | 530/391.5 |
| 5,120,526 | 6/1992 | Fritzberg et al. | 424/1.1 |
| 5,164,176 | 11/1992 | Gustavson et al. | 424/1.1 |
| 5,175,257 | 12/1992 | Kasina et al. | 530/391.5 |
| 5,175,343 | 12/1992 | Fritzberg et al. | 560/145 |
| 5,187,264 | 2/1993 | Verbruggen | 534/14 |
| 5,196,515 | 3/1993 | Lever et al. | 530/363 |
| 5,202,451 | 4/1993 | Fritzberg et al. | 556/419 |
| 5,349,066 | 9/1994 | Kaneko et al. | 546/294 |
| 5,554,357 | 9/1996 | Rajagopalan | 424/9.365 |
| 5,574,140 | 11/1996 | Pollack et al. | 534/10 |

FOREIGN PATENT DOCUMENTS

| | | |
|---|---|---|
| 93/02713 | 2/1983 | WIPO . |
| 89/07456 | 8/1989 | WIPO . |
| 91/16076 | 10/1991 | WIPO . |
| 92/10214 | 6/1992 | WIPO . |
| 92/10465 | 6/1992 | WIPO . |
| 92/10466 | 6/1992 | WIPO . |
| 92/19274 | 11/1992 | WIPO . |
| 92/21383 | 12/1992 | WIPO . |

OTHER PUBLICATIONS

Schneider et al., *J. Nuc. Med.*, vol. 25(2), pp. 223–29 1984.

Brenner, D. et al., "Synthesis and Characterization of a Series of Isomeric Oxotechnetium(V) Diamido Dithiolates", *Inorg. Chem.* 23: pp. 3793–3797 (1984).

Cotsyfakis, C. et al., "Indium–111–Labelled Cationic Complexes of Aminothiols: Structure–Activity Correlation", *European Journal of Nuclear Medicine*, 20: pp. 302–307 (Apr. 1993).

Eckelman, W. C. et al., "Three Approaches to Radiolabeling Antibodies with 99m Tc" *Nucl. Med. Biol.* 16: pp. 171–176 (1989).

Fischman, Alan J. et al., "Imaging Focal Sites of Bacterial Infection in Rats with Indium–111–Labeled Chemotactic Peptide Analogs", *Journal of Nuclear Medicine*, 32: pp. 483–494 (Mar. 1991).

Fritzberg, Alan R. et al., "Approaches to Radiolabeling of Antibodies for Diagnosis and Therapy of Cancer",*Pharmaceutical Research*, 5: pp. 325–334 (1988).

Olsen, R. K., "Synthesis of Quinoxaline Peptides by the Solid Phase Method", *J. Heterocycl Chem.* 7(2): pp. 435–437 (1970).

Paik, Chang H. et al., "The Labeling of High Affinity Sites of Antibodies with $^{99m}$Tc", *Journal of Nuclear Medicine*, 12: pp. 3–8 (1985).

Schneider, R. F., et al., "N,N'–bis(S–Benzoylmercaptoacetamido) Ethylenediamine and Propylenediamine Ligands as Renal Function Imaging Agents", *Journal of Nuclear Medicine*, 25: pp. 223–229 (1984).

*Primary Examiner*—Gary E. Hollinden
*Assistant Examiner*—Michael G. Hartley
*Attorney, Agent, or Firm*—Foley & Lardner

[57] ABSTRACT

Radionuclide chelating compounds are provided for conjugation to targetting molecules such as proteins, peptides or antibodies. The resulting labelled targetting molecules may be used in diagnosis and therapy.

19 Claims, No Drawings

HYDRAZINO-TYPE N₂S₂ RADIONUCLIDE CHELATING COMPOUNDS

This application is a continuation-in-part of U.S. Ser. No. 08/274,850 filed Jul. 14, 1994, now U.S. Pat. No. 5,574,140, which is a divisional of U.S. Ser. No. 08/116,504, filed Sep. 3, 1993, now abandoned.

FIELD OF THE INVENTION

This invention is in the field of diagnostic imaging, and relates to chemical chelators useful in the radiolabelling of agents that target tissues of diagnostic interest.

BACKGROUND TO THE INVENTION

The art of diagnostic imaging exploits contrasting agents that in binding or localizing site selectively within the body, help to resolve the image of diagnostic interest. $^{67}$Gallium salts, for example, have an affinity for tumours and infected tissue and, with the aid of scanning tomography, can reveal afflicted body regions to the physician. Other contrasting agents include the metal radionuclides such as $^{99m}$technetium and $^{186/188}$rhenium, and these have been used to label targetting molecules, such as proteins, peptides and antibodies that localize at desired regions of the human body.

As targetting agents, proteins and other macromolecules can offer the tissue specificity required for diagnostic accuracy; yet labelling of these agents with metal radionuclides is made difficult by their physical structure. Particularly, protein and peptide targetting agents present numerous sites at which radionuclide binding can occur, resulting in a product that is labelled heterogeneously. Also, and despite their possibly large size, proteins rarely present the structural configuration most appropriate for high affinity radionuclide binding, i.e. a region incorporating four or more donor atoms that form five-membered rings. As a result, radionuclides are bound typically at the more abundant low-affinity sites, forming unstable complexes. To deal with the problem of low affinity binding, Paik et al (Nucl Med Biol 1985, 12:3) proposed a method whereby labelling of antibodies is performed in the presence of excess DPTA (diaminetrimethylenepentaacetic acid), to mask the low affinity binding sites. While the problem of low affinity binding is alleviated by this method, actual binding of the radionuclide, in this case technetium, was consequently also very low. The direct labelling of proteins having a high proportion of cysteine residues also has been demonstrated (Dean et al; WO 92/13,572). This approach exploits thiol groups of cysteine residues as high-affinity sites for radionuclide binding, and is necessarily limited in application to those targetting agents having the required thiol structure.

A promising alternative to the direct labelling of targeting agents is an indirect approach, in which targeting agent and radionuclide are conjugated using a chelating agent. Candidates for use as chelators are those compounds that bind tightly to the chosen metal radionuclide and also have a reactive functional group for conjugation with the targetting molecule. For utility in diagnostic imaging, the chelator desirably has characteristics appropriate for its in vivo use, such as blood and renal clearance and extravascular diffusibility.

SUMMARY OF THE INVENTION

The present invention provides chelators that bind diagnostically and therapeutically useful metal radionuclides, and can be conjugated to targetting agents capable of localizing at body sites of diagnostic and therapeutic interest. The chelators of the present invention are peptide analogues designed structurally to present an $N_2S_2$ configuration capable of binding oxo, dioxo and nitrido ions of $^{99m}$technetium and $^{186/188}$rhenium.

More particularly, and according to one aspect of the invention, there are provided metal radionuclide chelators of the formula:

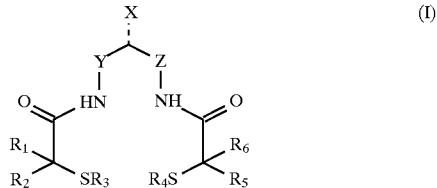

wherein $R_1$, $R_2$, $R_5$ and $R_6$ are independently selected from H; carboxyl; lower alkyl; and lower alkyl substituted with a group selected from hydroxyl, sulfhydryl, halogen, carboxyl and aminocarbonyl; or $R_8$; or $R_9$;

$R_3$ and $R_4$ are independently selected from H or a sulfur protecting group;

—X is selected from =O, =S, =CH$_2$, =NH$_2^+$ or —NHR$_8$ or —NHR$_9$;

Y and Z are independently selected from the group $CR_1R_2$ or $NR_7$;

$R_7$ is selected from H, carboxyl, lower alkyl and lower alkyl substituted with hydroxyl, carboxyl and halogen;

$R_8$ is a conjugating group; and $R_9$ is a targeting molecule.

According to another aspect of the invention, the chelators of the above formula are provided in a form having the metal radionuclide complexed therewith.

In another aspect of the invention, the chelator is provided in a form coupled to a diagnostically useful targeting molecule, and optionally in combination with a complexed metal radionuclide, for imaging use.

DETAILED DESCRIPTION OF THE INVENTION

The invention provides metal radionuclide chelators that when complexed with a radionuclide and conjugated to a targetting molecule are useful for delivering the radionuclide to a body site of therapeutic or diagnostic interest. As illustrated in the above formula, the chelators have an $N_2S_2$ configuration in which the radionuclide is complexed Terms defining the variables $R_1$–$R_7$ as used hereinabove have the following meanings:

"alkyl" refers to a straight or branched $C_1$–$C_8$ chain and embraces the term "lower alkyl" which refers to a straight or branched chain $C_1$–$C_3$ chain:

"halogen" refers to F, Cl, Br and I;

"sulfur protecting group" refers to a chemical group that inhibits oxidation, in particular those that are cleaved upon chelation of the metal. Sulfur protecting groups include known alkyl, aryl, acyl, alkanoyl, aryloyl, mercaptoacyl and organothio groups.

In preferred embodiments of the invention, the chelators conform to the above formula in which:

$R_1$, $R_2$, $R_5$ and $R_6$ are independently selected from H and a lower alkyl group selected from ethyl, propyl and most preferably methyl;

$R_3$ and $R_4$ are a hydrogen atom or a sulfur protecting group selected from benzoyl, acetamidomethyl and substituted or unsubstituted tetrahydropyranyl groups;

—X is selected from $=O$, $=S$, $=NH_2^+$, $—NHR_8$ and $—NHR_9$;

Y and Z are, independently, $NR_7$; and $R_7$ is selected from carboxyl, lower alkyl and preferably hydrogen.

Chelators having achiral carbon centres will advantageously alleviate the problems associated with differing biodistribution of various stereoisomers. In order to maintain achirality, a conjugating group must be attached to chelators of the invention at X. Attachment of a conjugating group, $R_8$, at X is most stable when X is the group $NH_2^+$. Accordingly, it is a preferred embodiment of the present invention to provide chelators having achiral carbon centres and have a conjugating $R_8$ group attached to an $NH_2^+$ group at X, to form the group $—NH—R_8$.

In specific embodiments of the invention, the chelators conform to the above general formula wherein $R_1$ is H or a sulfur protecting group; $R_1$, $R_2$, $R_5$ and $R_6$ are each H; X is O, S, $CH_2$ or $NH_2^+$; and Y and Z are $CH_2$ or NH. Specific examples include:

N,N'-bis-(S benzoylmercaptoacetyl)-carbohydrazide,

N,N'-bis-(S-Benzoylmercaptoacetyl)-1,3-diaminoguanidine hydrochloride, and the guanidinehydrazido form derivatized by a targeting molecule or by a conjugating group to which a targetting molecule is coupled, N,N'-bis-(S-benzoylmercaptoacetyl)-1,3-diaminoacetone, and N,N'-bis-(S-benzoylmercaptoacetyl)-1,3-thiocarbohydrozide.

For coupling to a targetting molecule, X or one of $R_1$, $R_2$, $R_5$ and $R_6$ desirably incorporates a "conjugating group" designated as $R_8$, a term used herein with reference to chemically reactive groups that can be coupled covalently to a selected targetting molecule. In the preferred case where the targetting molecule is a peptide or protein, the conjugating $R_8$ group is reactive under conditions that do not denature or otherwise adversely affect the peptide or protein. In one embodiment of the invention, the conjugating group is reactive with a functional group of the peptide/protein such as an amino terminal group or an ε-amino group of a lysine residue so that the reaction can be conducted in a substantially aqueous solution, Useful conjugating groups include but are not limited to carboxyl groups, activated esters, carboxy-methyl thio group, thiocyanates, amines, hydrazines, maleimides, thiols, and activated halides. In a preferred embodiment of the invention, conjugating groups are selected from methyl propanoate, carboxyl group and N-hydroxysuccinimide ester. Carboxyl conjugating groups may be activated with carbodiimide and an alcohol to form an active ester that is reactive with an amino group available on such targeting molecules as peptides and amino sugars, to form an amide bond.

In certain embodiments, chelators of the present invention are provided wherein X is a $CH_2$ or oxo group. In a preferred embodiment, X forms an $NH_2^+$ group that may have a conjugating group attached thereto forming the group $NH—R_8$. A conjugating $R_8$ group may be introduced to this type of chelator during standard synthesis of a diaminoguanidine intermediate. Briefly, thiocarbohydrazine is converted to methyl-thiocarbohydrazine by substitution with methyl iodide. Addition of a selected amino-substituted conjugating group to the methyl-thiocarbohydrazine results in an intermediate which is subsequently employed in the preparation of chelators wherein X is NH having a conjugate bound thereto. A method of preparing such a conjugate bound intermediate, is represented below.

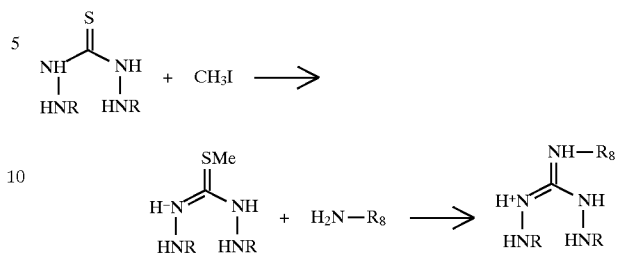

Chelators of the present invention that are symmetrical, that is $R_1$ and $R_2$ correspond to $R_5$ and $R_6$ respectively, can be prepared by the following general procedure, Commercially available iodoacetic acid, or a variant thereof substituted as desired, is reacted with potassium thiobenzoate yielding benzoylmercaptoacetic acid. This intermediate is then transformed into the corresponding N-hydroxysuccinimide ester using dicyclocarbodiimide in dioxane. The active ester is reacted in dioxane at room temperature with a selected carbohydrazide or diaminoguanidine or diaminoacetone. The resulting chelator is then purified by recrystallization.

A method of preparing the present symmetrical chelators is represented below:

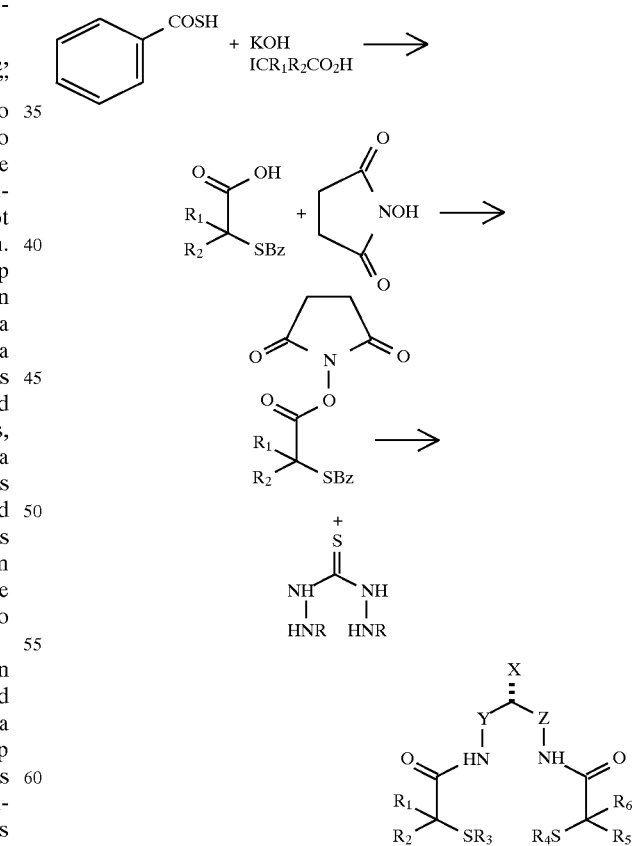

Preparation of chelators of the present invention that are not symmetrical, that is $R_1$ and $R_2$ do not correspond to $R_5$ and $R_6$, requires additional steps. In general, benzoylmercaptoacetyl-N-hydroxysuccinimide (formula II), the preparation of which is described above is reacted with a selected thiocarbohydrazide, carbohydrazide, diaminoguanidine or diaminoacetone of the general formula

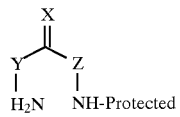

wherein one of the amino groups is N-protected. The resulting benzoylmercaptoacetyl-carbohydrazide/-diaminoguanidine/-diaminoacetone/-thiocarbohydrazide is deprotected and subsequently reacted with a benzoylmercaptoacetyl-N-hydroxysuccinimide having the selected $R_5$ and $R_6$ groups to yield the asymmetrical $N_2S_2$ chelator.

In a particular embodiment of the present invention, an N-protected diaminoguanidine is prepared from a hydrazine ester in which the OR group of the ester is substituted with an N-protected hydrazine to give the mono-N-protected diaminoguanidine. N-protecting groups common to the art may be used, for example t-butyloxycarbonyl (t-Boc) or 9-fluorenylmethyloxycarbonyl (Fmoc). Removal of t-Boc protecting groups can be achieved by addition of an anhydrous acid such as HCl in acetic acid while Fmoc may be cleaved with piperidine and diiodomethane or piperidine dimethylformamide.

Chelators of the present invention may also be asymmetrical with respect to Y and Z. That is one of Y or Z may be the group $CR_1R_2$ while the other is $NR_7$. This type of asymmetry may be introduced by using the intermediate 1,3-diaminoamidine or a derivative thereof in place of the intermediate 1,3-diaminoguanidine in the synthetic processes previously described.

It is to be understood that variation at $R_1$, $R_2$, $R_5$ and $R_6$ can be introduced by using variants of iodo acetic acid. For example the alpha carbon may have one or two substituents as well as iodine such as lower alkyl, substituted lower alkyl or a conjugating group. Variation at Y and Z may be introduced by using derivatives of carbohydrazide, diamino guanidine and diamino acetone. For example carbohydrazide and diamino guanidine intermediates may have carboxyl, lower alkyl, substituted lower alkyl or a conjugating $R_8$ group at either or both alpha nitrogens while diamino acetone may also have carboxyl; lower alkyl; substituted lower alkyl or a conjugating $R_8$ group at either or both alpha carbons.

A method of preparing the present asymmetric chelators is represented below:

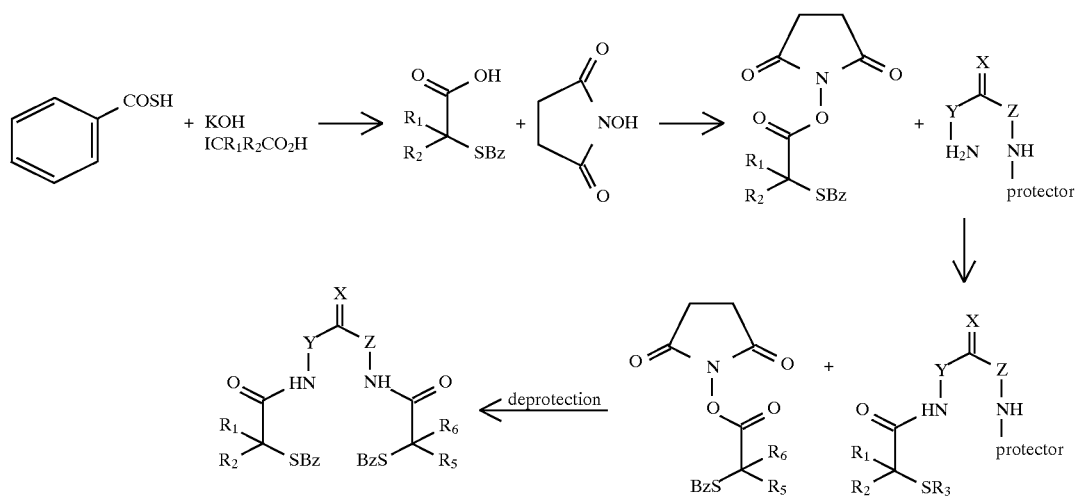

For diagnostic imaging purposes, the chelators are used in combination with a metal radionuclide. Suitable radionuclides include technetium and rhenium in their various forms such as $^{99m}TcO^{3-}$, $^{99m}TcO_2^+$, $ReO^{3+}$ and $ReO_2^+$. More desirably, the chelator is coupled through its conjugating group to a targetting $H_9$ molecule that serves to localize the chelated radionuclides to a desired location in a mammal. Examples of $R_9$ targetting molecules include, but are not limited to, steroids, proteins, peptides, antibodies, nucleotides and saccharides. Preferred targetting molecules include proteins and peptides, particularly those capable of binding with specificity to cell surface receptors characteristic of a particular pathology. For instance, disease states associated with over-expression of particular protein receptors can be imaged by labelling that protein or a receptor binding fragment thereof in accordance with the present invention. Peptide-based targetting molecules can be made, either per se or as chelator conjugates, by various known methods or in some instances can be commercially obtained. Solid phase synthesis employing alternating t-Boc protection and deprotection is the preferred method of making short peptides which can be an automated process. Recombinant DNA technology is preferred for producing proteins and long fragments thereof. The chelators of the present invention can be coupled to a targetting molecule prior to labelling with the radionuclide, a process referred to as the "bifunctional chelate" method. An alternative approach is the "prelabelled ligand" method in which the chelator is first labelled with a radionuclide and is then coupled to the targetting molecule.

Chelation of the selected radionuclide can be achieved by various methods. A chelator solution is formed initially by dissolving the chelator in aqueous alcohol eg. ethanol-water 1:1. The solution is degassed with nitrogen to remove oxygen then sodium hydroxide is added to remove the thiol protecting group. The solution is further purged with nitrogen and heated on a water bath to hydrolyse the thiol protecting group, and the solution is then neutralized with an organic acid such as acetic acid (pH 6.0–6.5). In the labelling step, sodium pertechnetate is added to the chelator solution with an amount of stannous chloride sufficient to reduce the technetium. The solution is mixed and left to react at room temperature and then heated on a water bath. In an alternative method, labelling can be accomplished as with the chelator solution adjusted to pH 8. Pertechnetate may be replaced with a solution of technetium complexed with labile ligands suitable for ligand exchange reactions with the desired chelator. Suitable ligands include tartarate, citrate or heptagluconate. Stannous chloride may be replaced with sodium dithionite as the reducing agent if the chelating solution is alternatively adjusted to pH 12–13 for the labelling step. The labelled chelator may be separated from contaminants $^{99m}TcO_4$ and colloidal $^{99m}TcO_2$ chromatographically, e.g., with a C-18 Sep Pak column activated with ethanol followed by dilute HCl. Eluting with dilute HCl separates the $^{99m}TcO_4$, and eluting with EtOH-saline 1:1 brings off the chelator while colloidal $^{99m}TcO_2$ remains on the column.

Once prepared the labelled chelator or conjugated chelator/targetting agent is administered to a patient by techniques common in the art of radiodiagnostic imaging or radiotherapy. Normally a labelled chelator solution is administered by injection intravenously, intra-arterially, peritoneally or intratumorally depending upon the particular site at which the radionuclide is desired. Typically, dosage for a human recipient will be about 5–50 mCi/70 kg and more typically in the range of 25–35 mCi/70 kg.

The following examples are presented to illustrate certain embodiments of the present invention.

EXAMPLE 1

Preparation of N,N'-bis(S-benzoylmercaptoacetyl)-carbohydrazide RP-021

To a purged stirring solution at 0° C. of (5.74 g, 41.6 mmoles) thiobenzoic acid in (100 mL) ethanol was added (27.8 mL, 3N, 83.2 mmoles) potassium hydroxide followed by (7.70 g, 41.6 mmoles) iodoacetic acid in (30 mL) ethanol. The solution stirred for 10 hours at room temperature under argon. The ethanol was rotavapped and the orange solid product was dissolved in (40 mL) water. The solution was acidified to pH 2.0 where an orange precipitate formed. This was filtered, washed with water, and dried in vacuo to give (7.98 g, 99% yield) benzoylmercaptoacetic acid.

To a stirring solution of (9.20 g, 46.9 mmoles) benzoylmercaptoacetic acid and (5.41 g, 46.9 mmoles) N-hydroxysuccinimide in (100 mL) dioxane was added a solution of (9.70 g, 47 mmoles) dicyclohexylcarbodiimide in (40 mL) dioxane. The reaction was stirred 12 hours followed by cooling to 4° C., filtering, and rotavapping off the dioxane to a white solid. The solid was triturated with cold isopropanol, filtered, and dried in vacuo yielding 10.8 g, 78% benzoylmercaptoacetyl-N-hydroxysuccinimide. 200 mg was recrystallized from 500 mg in hot ethyl acetate.

To a stirring solution of (1.17 g, 4.0 mmoles) benzoylmercaptoacetyl-N-hydroxysuccinimide in (36 mL) dioxane was added a solution of (180 mg, 2.0 mmoles) carbohydrazide in (10 mL) dioxane. After 1 hour TLC showed a partial reaction and (404 mg, 4.0 mmoles) triethylamine was added. The reaction stirred 4 hours followed by rotavapping off the dioxane and adding (5 mL) water to a white solid. This was filtered, washed with (5 mL) water, and dried in vacuo yielding 772 mg, 86.5% N,N'-bis-(S-benzoylmercaptoacetyl)-carbohydrazide (m.p. 184°–190° C.).

EXAMPLE 2

Preparation of N,N'-bis-(S-benzoylmercaptoacetyl)-1,3-diaminoguanidine hydrochloride RP-032

To a purged stirring solution at 0° C. of (5.74 g, 41.6 mmoles) thiobenzoic acid in (100 mL) ethanol was added (27.8 mL, 3N, 83.2 mmoles) potassium hydroxide followed by (7.70 g, 41.6 mmoles) iodoacetic acid in (30 mL) ethanol. The solution stirred for 10 hours at room temperature under argon. The ethanol was rotavapped and the orange solid product was dissolved in (40 mL) water. The solution was acidified to pH 2.0 where an orange precipitate formed. This was filtered, washed with water, and dried in vacuo to give (7.98 g, 99% yield) benzoylmercaptoacetic acid.

To a stirring solution of (9.20 g, 46.9 mmoles) benzoylmercaptoacetic acid and (5.41 g, 46.9 mmoles) N-hydroxysuccinimide in (100 mL) dioxane was added a solution of (9.70 g, 47 mmoles) dicyclohexylcarbodiimide in (40 mL) dioxane. The reaction was stirred 12 hours followed by cooling to 4° C., filtering, and rotavapping off the dioxane to a white solid. The solid was triturated with cold isopropanol, filtered, and dried in vacuo yielding 10.8 g, 78% benzoylmercaptoacetyl-N-hydroxysuccinimide. 200 mg was recrystallized from 500 mg in hot ethyl acetate.

To a stirring solution of (200 mg, 1.59 mmoles) 1,3-diaminoguanidine.HCl in (3 mL) methanol was added a solution of (936 mg, 3.19 mmoles) benzoylmercaptoacetyl-N-hydroxysuccinimide and (322 mg, 3.19 mmoles) triethylamine in (30 mL) dioxane. The reaction stirred 14 hours overnight forming a fine white precipitate. The solvents were rotavapped off to a sticky white solid. The solid was triturated with cold isopropanol, filtered, washed with isopropanol, and dried in vacuo yielding 155 mg, 32% N,N'-bis-(S-benzoylmercaptoacetyl)-1,3-diaminoguanidine hydrochloride (m.p. 126°–128° C.).

EXAMPLE 3

Preparation of N,N'-bis-(S-benzoylmercaptoacetyl)-1,3-diaminoacetone RP 042

To a purged stirring solution at 0° C. of (5.74 g, 41.6 mmoles) thiobenzoic acid in (100 mL) ethanol was added (27.8 mL, 3N, 83.2 mmoles) potassium hydroxide followed by (7.70 g, 41.6 mmoles) iodoacetic acid in (30 mL) ethanol. The solution stirred for 10 hours at room temperature under argon. The ethanol was rotavapped and the orange solid product was dissolved in (40 mL) water. The solution was acidified to pH 2.0 where an orange precipitate formed. This was filtered, washed with water, and dried in vacuo to give (7.98 g, 99% yield) benzoylmercaptoacetic acid.

To a stirring solution of (9.20 g, 46.9 mmoles) benzoylmercaptoacetic acid and (5.41 g, 46.9 mmoles)

N-hydroxysuccinimide in (100 mL) dioxane was added a solution of (9.70 g, 47 mmoles) dicyclohexylcarbodiimide in (40 mL) dioxane. The reaction was stirred 12 hours followed by cooling to 4° C., filtering, and rotavapping off the dioxane to a white solid. The solid was triturated with cold isopropanol, filtered, and dried in vacuo yielding 10.8 g, 78% benzoylmercaptoacetyl-N-hydroxysuccinimide. 200 mg was recrystallized from 500 mg in hot ethyl acetate.

To a stirring solution of (492 g, 1.68 mmoles) benzoylmercaptoacetyl-N-hydroxysuccinimide and (150 mg, 0.84 mmoles) 1,3-diaminoacetone hydrochloride monohydrate in (15 mL) dioxane was added (850 mg, 8.40 mmoles) triethylamine. The reaction stirred 3.5 days followed by rotavapping off the dioxane to a yellow oil and adding (3 mL) water to a yellow solid. The solid was crushed, filtered, washed with water, and dried in vacuo yielding 242 mg, 65% N,N'-bis-(S-benzoylmercatoacetyl)1, 3-diaminoacetone (m.p. 134°–140° C.).

EXAMPLE 3B

Preparation of N,N'-bis-(S-benzoylmercatoacetyl)-1, 3-thiocarbohydrazide

To a stirring solution of (2 eq) benzoylmercaptoacetyl-N-hydroxy-succinimide in dioxane is added a solution of (1 eq) thiocarbohydrazide in dioxane followed by (2 eq) triethylamine. The reaction is stirred at room temperatuare for 4 hours where the solvent is evaporated under reduced pressure and water is added. The resulting solid is filtered, washed with water and dried in vacuo to yield N,N'-bis-(S-benzoylmercatoacetyl)-carbohydraxide.

EXAMPLE 4

Preparation of $^{99m}$Tc Labelled Chelators

Approximately 1 mg of each chelator was dissolved in 200 μL saline or 200 μL ethanol:water (1:1) in a tube. To the tube was added 100–300 μL sodium $^{99m}$Tc-pertechnetate (5–15 mCi), 100 μL phosphate buffer (0.25M, pH 7.4), and 200 μL of a solution containing 50 μg stannous chloride dihydrate and 40 mg sodium tartrate dihydrate. The tube was capped tightly and placed in a boiling water bath for 10 minutes.

After cooling, the reaction mixture was loaded onto a C-18 solid-phase extraction cartridge (Sep-Pak) which had been activated with 5 mL methanol and 5 mL 1 mM HCl. The cartridge was washed with 5 mM HCl and the eluate was collected in a test tube. The cartridge was then dried by forcing air through it. The product was eluted with 2 mL ethanol:water (1:1) and collected in a separate tube. The cartridge was placed in another tube and the three tubes were assayed in a radionuclide dose calibrator (ionization chamber). The yield was calculated as the activity in the ethanol:water eluate divided by the total activity in the three tubes under the assumption that the desired product was relatively lipophilic. A less lipophilic chelator would elute partially in the acid wash and the apparent yield would be low.

| Labelling yields | | | |
|---|---|---|---|
| Example 1 | 57% | 59% | 39% |
| Example 2 | 31% | 25% | 58% |
| Example 3 | 76% | 75% | |

EXAMPLE 5

In Vivo Distribution

Distribution within rats of selected chelators and a reference chelator were determined using established protocols. Briefly, male Wistar rats (Charles River, 200 g) were anaesthetized with somnitol (40 to 50 mg/kg) and 200 μL of the labelled chelator (ie. 200 μCi) was injected intravenously via the tail vein. Serial whole-body scintigrams were acquired for first 10 minutes, After further images were obtained at 60 and 120 minutes, the rat was killed with anaesthesia and samples of organs (blood, heart, lung, liver, spleen, kidney, muscle, GI tract) were weighed and counted in either a well-type gamma counter or in a gamma dose calibrator. Dose calculations were made based on the assumption that rats weighed 200 g and that the blood volume constituted 8% body weight. All results were corrected for the residual dose in the tail.

Each of the present chelators examined cleared relatively rapidly from the blood as desired. For the chelator of example 1, it was found that the GI tract excretion was remarkably low [in comparison with the $N_2S_2$ reference chelator]. The GI tract accounted for about 9% of the dose, and only about 14% remaining in the blood. The chelator of example 2 localized primarily (30%) in the GI tract and (20%) in urine, with only about 10% of the dose remaining in the blood. The chelator of example 3 also localized primarily (50%) in the GI tract and (25%) in urine with only 3% in the blood.

Of these chelators, the chelator of example 3 showed the fastest clearance from the blood and other tissues and is mainly eliminated through the liver and GI tract. The chelators of example 1 and 2 had approximately equal accumulation in the kidney (7–14%).

We claim:

1. A compound of the general formula:

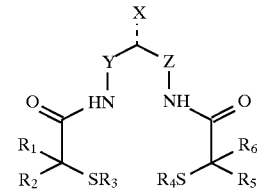

wherein $R_1$, $R_2$, $R_5$ and $R_6$ are independently selected from the group consisting of H; carboxyl; lower alkyl; lower alkyl substituted with a group selected from the group consisting of hydroxyl, sulfhydryl, halogen, carboxyl and aminocarbonyl; $R_8$; or $R_9$;

$R_3$ and $R_4$ are independently selected from the group consisting of H or a sulfur protecting group;

—X is selected from the group consisting of =O, =S, =CH$_2$, =NH$_2$, —NHR$_8$, or NHR$_9$;

Y and Z are both NR$_7$;

$R_7$ is selected from the group consisting of H, carboxyl, $C_{1-3}$ alkyl or $C_{1-3}$ alkyl substituted with a group selected from the group consisting of hydroxyl, carboxyl, or halogen;

$R_8$ is a conjugating molecule; and $R_9$ is a targeting molecule.

2. A compound according to claim 1, wherein —X is =O or =S.

3. A compound according to claim 2, wherein $R_1$, $R_2$, $R_5$ and $R_6$ are hydrogen.

4. A compound according to claim 3, wherein $R_7$ is hydrogen.

5. A compound according to claim 1, which is selected from:

N,N'-bis-(S benzoylmercaptoacetyl)-carbohydrazide
N,N'-bis-(S-Benzoylmercaptoacetyl)-1,3-diaminoguanidine hydrochloride
N,N'-bis-(S-benzoylmercaptoacetyl)-1,3-diaminoacetone
N,N'-bis-(S-benzoylmercaptoacetyl)-1,3-thiocarbohydrazide.

6. A compound according to claim 1, wherein $R_3$ and $R_4$ are selected from the group consisting of a hydrogen atom, benzoyl group, an acetamidomethyl group and a substituted or unsubstituted tetrahydropyranyl group.

7. A compound according to claim 1, in a form complexed with a metal radionuclide or an oxide or nitride thereof.

8. A compound according to claim 1, in a form complexed with $^{99m}Tc$ or an oxide thereof.

9. A compound of the general formula:

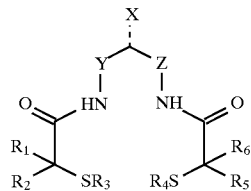

wherein
$R_1$, $R_2$, $R_5$ and $R_6$ are independently selected from the group consisting of H; carboxyl; lower alkyl; lower alkyl substituted with a group selected from the group consisting of hydroxyl, sulfhydryl, halogen, carboxyl and aminocarbonyl; $R_8$; or $R_9$;
$R_3$ and $R_4$ are independently selected from the group consisting of H or a sulfur protecting group;
—X is selected from the group consisting of =O, =S, =CH$_2$, =NH$_2$, —NHR$_8$, or NHR$_9$;
Y and Z are both NR$_7$;
$R_7$ is selected from the group consisting of H, carboxyl, $C_{1-3}$ alkyl or $C_{1-3}$ alkyl substituted with a group selected from the group consisting of hydroxyl, carboxyl, or halogen;
$R_8$ is a conjugating molecule; and
$R_9$ is a targeting molecule,
wherein at least one of $R_1$, $R_2$, $R_5$, or $R_6$ is $R_8$ or $R_3$ or X is —NH—$R_8$ or —NH—$R_9$.

10. A compound according to claim 9, wherein $R_8$ is selected from the group consisting of carboxyl, N-hydroxysuccinimide ester and methyl propanoate.

11. A compound according to claim 10 wherein $R_1$, $R_2$, $R_5$, and $R_6$ are hydrogen and X is —NHR$_8$ or —NHR$_9$.

12. A compound according to claim 10, wherein X is NH$_2^+$.

13. A compound according to claim 12, in a form complexed with a metal radionuclide or an oxide or nitride thereof.

14. A compound according to claim 13, in a form complexed with $^{99m}Tc$ or oxide thereof.

15. A compound of the general formula:

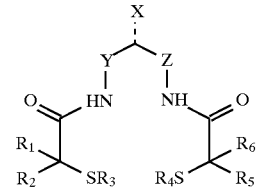

wherein
$R_1$, $R_2$, $R_5$ and $R_6$ are independently selected from H; carboxyl; lower alkyl; and lower alkyl substituted with a group selected from hydroxyl, sulfhydryl, halogen, carboxyl and aminocarbonyl; or $R_8$; or $R_9$;
$R_3$ and $R_4$ are independently selected from H and a sulfur protecting group;
—X is selected from =O, =S, =CH$_2$, =NH$_2$ or —NHR$_8$ or —NHR$_9$;
Y and Z are both NR$_7$;
$R_7$ is selected from H, carboxyl, $C_{1-3}$ alkyl and $C_{1-3}$ alkyl substituted hydroxyl, carboxyl and halogen;
$R_8$ is a conjugating group; and
$R_9$ is a targeting molecule;
wherein at least one of $R_1$, $R_2$, $R_5$ and $R_6$ is $R_9$ or X is —NHR$_9$.

16. A compound according to claim 15, wherein $R_1$, $R_2$, $R_5$ and $R_6$ are H; and X is —NHR$_9$.

17. A compound according to claim 16, wherein $R_9$ is a protein or peptide.

18. A compound according to claim 16, in a form complexed with a metal radionuclide or an oxide or nitride thereof.

19. A compound according to claim 18, in a form complexed with $^{99m}Tc$ or oxide thereof.

* * * * *

UNITED STATES PATENT AND TRADEMARK OFFICE
CERTIFICATE OF CORRECTION

PATENT NO. : 5,858,327
DATED : January 12, 1999
INVENTOR(S) : Pollak et al.

It is certified that error appears in the above-identified patent and that said Letters Patent is hereby corrected as shown below:

Column 11,
Line 42, should read -- wherein at least one of $R_1$, $R_2$, $R_5$, or $R_6$ is $R_8$ or $R_9$ or X --

Signed and Sealed this

Second Day of August, 2005

JON W. DUDAS
*Director of the United States Patent and Trademark Office*